(12) United States Patent
Hiskey et al.

(10) Patent No.: US 6,342,589 B1
(45) Date of Patent: Jan. 29, 2002

(54) PREPARATION OF 3,3'-AZOBIS(6-AMINO-1, 2,4,5-TETRAZINE)

(75) Inventors: Michael A. Hiskey, Los Alamos; David E. Chavez, Rancho de Taos; Darren Naud, Los Alamos, all of NM (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 09/814,110

(22) Filed: Mar. 22, 2001

(51) Int. Cl.[7] ...................... C07C 245/04; C07C 291/08
(52) U.S. Cl. .................. 534/567; 534/586; 534/767
(58) Field of Search ................................ 534/567, 767, 534/586

(56) References Cited

PUBLICATIONS

Chavez et al., Angew. Chem. Int. Ed., 2000, 39(10), 1791–1793.*

\* cited by examiner

Primary Examiner—Fiona T. Powers
(74) Attorney, Agent, or Firm—Bruce H. Cottrell; Dickson G. Kehl; Virginia B. Caress

(57) ABSTRACT

The compound of the structure

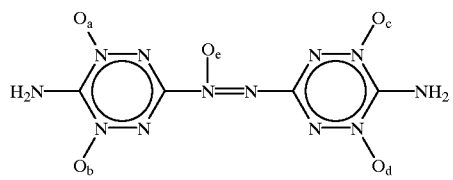

where a, b, c, d and e are 0 or 1 and a+b+c+d+e is from 0 to 5 is disclosed together with the species 3,3'-azobis (6-amino-1,2,4,5-tetrazine) and a process of preparing such compounds.

10 Claims, No Drawings

PREPARATION OF 3,3'-AZOBIS(6-AMINO-1, 2,4,5-TETRAZINE)

FIELD OF THE INVENTION

The present invention relates generally to an energetic material and more particularly to a high nitrogen energetic material. This invention was made with government support under Contract No. W-7405-ENG-36 awarded by the U.S. Department of Energy. The government has certain rights in the invention.

BACKGROUND OF THE INVENTION

High-nitrogen compounds form a unique class of energetic materials deriving most of their energy from their very high positive heats of formation rather than from oxidation of the carbon backbone, as with traditional energetic materials. The high nitrogen content typically leads to high densities, and the low amount of hydrogen and carbon also allows for a good oxygen balance to be achieved more easily. Oxygen balance is a measure of the oxygen/fuel ratio in a compound. It has been previously demonstrated that high-nitrogen materials can show remarkable insensitivity to electrostatic discharge, friction, and impact.

Tetrazine rings linked by an azo group are practically nonexistent. The only synthesis of azo-1,2,4,5-tetrazines in the literature was reported by Russian scientists in 1971 and 1990. Although they describe the preparation of 3,3'-azobis (6-phenyl-1,2,4,5-tetrazine) and 3,3'-azobis[6-(4-chlorophenyl)-1,2,4,5-tetrazine], no physical properties or proof of structure were given for the compounds.

SUMMARY OF THE INVENTION

In accordance with the purposes of the present invention, as embodied and broadly described herein, the present invention includes as a composition of matter, the compound of the formula

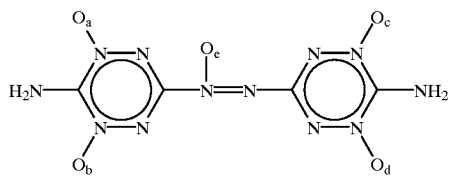

where a, b, c, d and e are 0 or 1 and a+b+c+d+e is from 0 to 5. The present invention further includes the species, 3,3'-azobis(6-amino-1,2,4,5-tetrazine), where a, b, c, d and e of the formula are each 0.

The present invention further includes a process of preparing 3,3'-azobis(6-amino-1,2,4,5-tetrazine) including reacting 3,6-bis(3,5-dimethylpyrazol-1-yl)-1,2,4,5-tetrazine with hydrazine to form a first intermediate product, reacting said first intermediate product with N-bromosuccinimide in acetonitrile to form a second intermediate product, reacting said second intermediate product with ammonia in DMSO to form a 3,3'-azobis(6-amino-1,2,4,5-tetrazine) DMSO solvate, and converting said 3,3'-azobis(6-amino-1,2,4,5-tetrazine) DMSO solvate to 3,3'-azobis(6-amino-1,2,4,5-tetrazine).

Still further, the present invention includes a process of preparing a compound of the formula

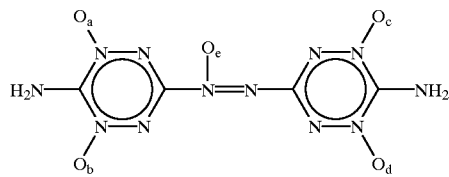

where a, b, c, d and e are 0 or 1 and a+b+c+d+e is from about 0.1 up to 5, comprising reacting 3,3'-azobis(6-amino-1,2,4,5-tetrazine) with an oxidizing agent for time and at temperatures sufficient to form said compound.

DETAILED DESCRIPTION

The present invention is concerned with the preparation of azo-1,2,4,5-tetrazines and in particular compounds of the formula

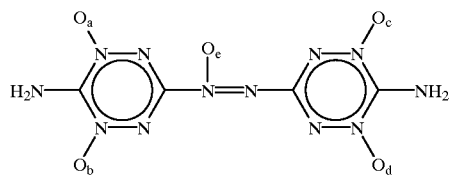

where a, b, c, d and e are 0 or 1 and a+b+c+d+e is from 0 to 5, and especially the compound 3,3'-azobis(6-amino-1,2,4,5-tetrazine) where a, b, c, d and e are 0. In one preferred embodiment of the compound, a+b+c+d+e is from about 3.0 to about 4.0 for ease of preparation.

Interest in the synthesis of azo-1,2,4,5-tetrazines followed from previous studies on azo-1,2,5-oxadiazoles. It was found that 327 kJmol$^{-1}$ of energy is gained in the transformation of 4,4'-hydrazobis-(1,2,5-oxadiazol-3-amine) to 4,4'-azobis(1,2,5-oxadiazol-3-amine). The latter material is a thermally stable, insensitive explosive. Extrapolating from these data, 3,3'-azobis(6-amino-1,2,4,5-tetrazine) would give an even higher heat of formation due to the intrinsically large heat of formation of the 1,2,4,5-tetrazine ring.

Previously it has been shown that oxidation of 3-amino-1,2,4,5-tetrazines leads to the formation of N-oxides in which the oxide moiety is α to the amino group. In the case of 3,6-diamino-1,2,4,5-tetrazine (R=NH$_2$), N-oxide groups are formed at the 1- and 4-positions, whereas with 3-amino-1,2,4,5-tetrazines (R=H), N-oxidation occurs at the two ring nitrogen atoms α to a nitro group when 3,6-diamino-1,2,4, 5-tetrazine is the substrate. Under no circumstances has the formation of an azo or azoxy linkage been observed. Thus it was recognized that the formation of the azo group must be accomplished by a different synthetic approach. Here, synthesis of 3,3'-azobis(6-amino-1,2,4,5-tetrazine) is described, as well as some of the properties of this high-nitrogen material.

The preparation of 3,3'-azobis(6-amino-1,2,4,5-tetrazine) was as follows. The 3,5-dimethylpyrazol-1-yl moieties of 3,6-bis(3,5-dimethylpyrazol-1-yl)-1,2,4,5-tetrazine have been shown to be good leaving groups in nucleophilic displacements on 1,2,4,5-tetrazines. With readily available 3,6-bis(3,5-dimethylpyrazol-1-yl)1,2,4,5-tetrazine as a starting material, a hydrazo compound was prepared by treatment of the 3,6-bis(3,5-dimethylpyrazol-1-yl)-1,2,4,5-tetrazine with 0.5 equivalents of hydrazine. Surprisingly, it was found that a variety of oxidizing reagents typically used to oxidize a hydrazo group to an azo moiety (oxidizing reagents such as $Br_2$, $NO_2$, $MnO_2$, HgO, and HONO) did not lead to the formation of the azo group. Oxidation was only achieved with N-bromosuccinimide (NBS), which also brominated the 3,5-dimethylpyrazol-1-yl rings to give an azo compound. The formation of the azo group was confirmed by the absence of signals and stretches for NH in the H NMR and IR spectra as well as elemental analysis. Treatment of the azo compound with ammonia in acetonitrile yielded a precipitate, which upon analysis showed that complete displacement of the 4-bromo-3,5-dimethylpyrazol-1-yl groups did not occur. However, when the reaction was conducted in dimethyl sulfoxide (DMSO) followed by treatment of the reaction mixture with 2-propanol, a red-brown precipitate was isolated.

According to NMR spectroscopy this material was the bis-DMSO solvate of 3,3'-azobis(6-amino-1,2,4,5-tetrazine); however, elemental analysis was inconsistent with the proposed structure, as is typical of compounds high in nitrogen. An X-ray crystal structure analysis of this material confirmed the structure to be the bis-DMSO solvate of 3,3'-azobis(6-amino-1,2,4,5-tetrazine), thus providing the evidence for the synthesis of an azo-1,2,4,5-tetrazine. A density of 1.526 g/cm was determined from the X-ray crystal structure. The molecules are in an E configuration (trans configuration) and form planar sheets despite the presence of DMSO molecules in the crystal. It was believed that this graphite-like structure would lead to a high density of the neat material. Indeed, a gas pyconmetry density of 1.78 g/cm was determined for pure 3,3'-azobis(6-amino-1,2,4,5-tetrazine), which is of a level equal to or greater than the most dense C,H,N molecule known (1.738 g/cm for 5,5-bi-1H-tetrazole).

The DMSO solvate was easily broken by treatment with boiling water to give pure 3,3'-azobis(6-amino-1,2,4,5-tetrazine). The pure material was found to be thermally stable up to 252° C. (differential scanning calorimetry), and the heat of formation was measured to be +862 $kJmol^{-1}$ by combustion calorimetry. This is a very high heat of formation and when normalized to a per atom value, a value of 43.1 kJ per atom is realized. Some sensitivity properties include a drop weight impact value of 70 cm (the value for the high-explosive HMX (octahydro-1,3,5,7-tetranitro-1,3,5,7-tetrazocine) is 25 cm), despite the fact that there are no oxygen atoms in the molecule. The compound was also found insensitive to initiation by spark (0.36 J) or friction (BAM, >36 kg).

Following preparation of the 3,3'-azobis(6-amino-1,2,4,5-tetrazine), it can be oxidized with various oxygen transfer reagents to form a compound of the formula

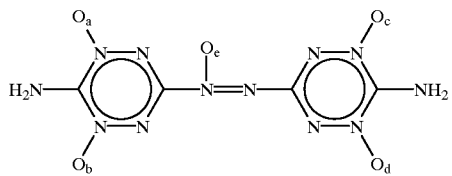

where a, b, c, d and e are 0 or 1 and a+b+c+d+e is from about 0.1 up to 5. In the formula, a+b+c+d+e is preferably greater than about 3. Repeated oxidation steps may be necessary to obtain values greater than about 3.2. In the shown structure, the oxygen to nitrogen bonds are dative bonds and thus no charges are shown. Oxidation can be accomplished by reaction of the 3,3'-azobis(6-amino-1,2,4,5-tetrazine) with trifluoroacetic anhydride in a heterogeneous mixture of hydrogen peroxide in methylene chloride. Other oxidizing may be used as well.

The present invention is more particularly described in the following examples which are intended as illustrative only, since numerous modifications and variations will be apparent to those skilled in the art.

EXAMPLE 1

Preparation of 3,3'-hydrazobis[6-(3,5-dimethylpyrazol-1-yl)]-1,2,4,5-tetrazine was as follows. To 3,6-bis(3,5-dimethylpyrazol-1-yl)-1,2,4,5-tetrazine (270.0 g, 1.0 mol) in 2-propanol (2 L) in a mechanically stirred 5-L, 3-necked flask was added anhydrous hydrazine (16.0 g, 0.5 mol) all at once with efficient stirring. The mixture was refluxed for 2 hours and allowed to cool and stir overnight. The orange product was filtered and washed with 2-propanol to give 143.0 g of pure 3,3'-hydrazobis[6-(3,5-dimethylpyrazol-1-yl)]-1,2,4,5-tetrazine. The mother liquor was allowed to stand for a few weeks and refiltered to provide an additional 7.3 g of product identical to the first crop (total yield 79%); m.p. 215–217° C., IR (KBr): $\bar{v}$=3194, 1575, 1490, 1415 $cm^{-1}$; $^1H$ NMR (270 MHz, $[D_6]DMSO$, 25° C., TMS): δ=2.21 (s,6H), 2.49 (s, 6H), 6.22 (s, 2H), 11.2 (brs, 2H); $^{13}C$ NMR 270 MHz, $[D_6]DMSO$, 25° C., TMS): δ=12.3, 13.0, 109.5, 142.3, 151.3, 158.9, 162.7; elemental analysis calculated for $C_{14}H_{16}N_{14}$: C, 44.21; H, 4.24; N, 51.55; found: C, 43.95; H, 4.40; N 51.39.

EXAMPLE 2

Preparation of 3,3'-azobis[6-(4-bromo-3,5-dimethylpyrazol-1-yl)]-1,2,4,5-tetrazine was as follows. N-Bromosuccinimide (267.4 g, 1.5 mol) was dissolved in acetonitrile (2 L) in a 5-L, 3-necked flask equipped with a mechanical stirrer. 3,3'-hydrazobis[6-(3,5-dimethylpyrazol-1-yl)]-1,2,4,5-tetrazine (143.0 g, 0.38 mol) was added portionwise over 15 minutes and the mixture was allowed to stir for 1 hour. The purple precipitated product was filtered and washed with tert-butyl methyl ether and air-dried to yield 197.0 g of 3,3'-azobis[6-(4-bromo-3,5-dimethylpyrazol-1-yl)]-1,2,4,5-tetrazine (98% yield); m.p. 195–197° C., IR (KBr): $\bar{v}$=1501, 1450 $cm^{-1}$; $^1H$ NMR (270 MHz, $CDCl_3$, 25° C., TMS): δ=2.44 (s,6H), 2.84 (s, 6H); $^{13}C$ NMR 270 MHz, $CDCl_3$, 25° C., TMS): δ=13.0, 14.4, 104.4, 142.2, 155.3, 159.3, 167.9; elemental analysis calculated for $C_{14}H_{12}N_{14}Br_2$: C, 31.36; H, 2.26; N, 36.57; found: C, 30.99; H, 2.21; N, 36.51.

EXAMPLE 3

Preparation of 3,3'-azobis(6-amino-1,2,4,5-tetrazine) was as follows. Ammonia was bubbled rapidly through DMSO (1 L) in a 4-L beaker until 7.0 g (0.41 mol) were absorbed. To this was added 3,3'-azobis[6-(4-bromo-3,5-dimethylpyrazol-1-yl)]-1,2,4,5-tetrazine (110.4 g, 0.206 mol) with stirring within 1 minute. The reaction mixture was allowed to stir for 15 minutes and then diluted with 2-propanol (1 L). The red solid was filtered, washed with 2-propanol, and air-dried to yield 34.3 g of 3,3'-azobis(6-amino-1,2,4,5-tetrazine) 2DMSO (44% yield). The material was boiled in water (250 mL) for a few minutes to break the DMSO solvate, filtered, washed and air-dried to give pure 3,3'-azobis(6-amino-1,2,4,5-tetrazine); m.p. 252 (decomp.), IR (KBr): $\bar{v}$=3372, 3283, 3194, 1629, 1506 $cm^{-1}$; $^1H$ NMR (270 MHz, $[D_7]DMF$, 25° C., TMS): δ=8.93 (br s,4H); $^{13}C$ NMR 270 MHz, $[D_7]DMF$, 25° C., TMS): δ=163.6, 167.9;

elemental analysis calculated for $C_4H_4N_{12}$: C, 21.82; H, 1.83; N, 76.35; found: C, 21.46; H, 2.11; N, 67.70.

EXAMPLE 4

Oxidation of 3,3'-azobis(6-amino-1,2,4,5-tetrazine) was as follows. To a heterogeneous mixture of 90% hydrogen peroxide (14.4 mL, 0.51 mol) in methylene chloride (400 mL) was added trifluoroacetic anhydride (82 mL, 0.57 mol) with stirring and cooling at 0° C. This reaction was allowed to stir for 10 minutes before the addition of 3,3'-azobis(6-amino-1,2,4,5-tetrazine) (10.0 g, 45 mmol). After four hours at 0° C., the temperature of the slurry-like mixture is ramped to 22° C. over 6 hours. The reaction is allowed to continue at 22° C. for 18 hours after which it is poured in 1 L of cold water. The mixture is filtered and washed with copious amounts of water and dried. The DAAT mixed N-oxides obtained contains about 19 to 21 percent oxygen by weight, or from 3.2 to 3.6 oxygen atoms per molecule. The calculated detonation velocity of this material (3.5 oxygen atoms per molecule, measured density of 1.88 g/cm³) is 9.0 km/s with a calculated detonation pressure of 366 kbar. Re-oxidizing this material using the above procedure yielded a product with 22 percent oxygen by weight, or 3.9 oxygen atoms per molecule. The neat material was sensitive to initiation by spark at less than 0.36 J and sensitive to initiation by friction (BAM at from 2–14 kg). It had a drop weight impact value of 20 cm. After the material was formulated with 5 percent by weight of polyvinyl alcohol and 1 percent by weight triethylene glycol, the formulation was also found insensitive to initiation by spark (0.36 J) or friction (BAM, at 17 kg). The present process allowed easy preparation of multigram quantities.

Additional details are contained in Angew. Chem. Int. Ed., 2000, 39, No. 10, pp. 1791–1793, such description expressly incorporated herein by reference.

Although the present invention has been described with reference to specific details, it is not intended that such details should be regarded as limitations upon the scope of the invention, except as and to the extent that they are included in the accompanying claims.

What is claimed is:

1. The compound of the formula

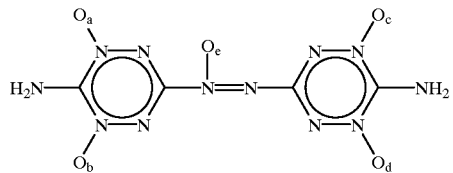

where a,b,c,d and e are 0 or 1 and a+b+c+d+e is from 0 to 5.

2. A mixture of compounds of the formula of claim 1 wherein a+b+c+d+e is from about 3.0 to about 4.0.

3. The compound of the formula of claim 1 wherein a, b, c, d and e are each zero such that the compound is 3,3'-azobis(6-amino-1,2,4,5-tetrazine).

4. A process of preparing 3,3'-azobis(6-amino-1,2,4,5-tetrazine) comprising:

reacting 3,6-bis(3,5-dimethylpyrazol-1-yl)-1,2,4,5-tetrazine with hydrazine to form a first intermediate product;

reacting said first intermediate product with N-bromosuccinimide to form a second intermediate product;

reacting said second intermediate product with ammonia in DMSO to form a 3,3'-azobis(6-amino-1,2,4,5-tetrazine) DMSO solvate;

converting said 3,3'-azobis(6-amino-1,2,4,5-tetrazine) DMSO solvate to 3,3'-azobis(6-amino-1,2,4,5-tetrazine).

5. The process of claim 2 wherein said conversion of 3,3'-azobis(6-amino-1,2,4,5-tetrazine) DMSO solvate to 3,3'-azobis(6-amino-1,2,4,5-tetrazine) is by boiling in water.

6. The process of claim 2 wherein said reaction of said first intermediate product with N-bromosuccinimide is conducted in acetonitrile.

7. The process of claim 2 wherein said reaction of 3,6-bis(3,5-dimethylpyrazol-1-yl)-1,2,4,5-tetrazine with hydrazine is conducted in propanol.

8. A process of preparing a compound of the formula

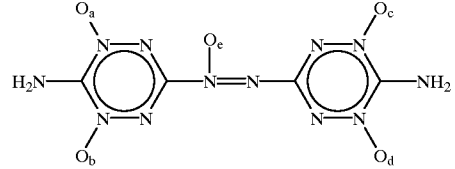

where a, b, c, d and e are 0 or 1 and a+b+c+d+e is from about 0.1 up to 5, comprising reacting 3,3'-azobis(6-amino-1,2,4,5-tetrazine) with an oxidizing agent for time and at temperatures sufficient to form said compound.

9. The process of claim 8 wherein a+b+c+d+e is from about 3.0 to about 4.0.

10. The process of claim 8 wherein said oxidizing agent is peroxytrifluoroacetic acid.

* * * * *